(12) United States Patent
Colachis et al.

(10) Patent No.: US 11,334,159 B2
(45) Date of Patent: May 17, 2022

(54) NON-VERBAL COMMUNICATIONS RADIO AND NON-VERBAL COMMUNICATION SYSTEM USING A PLURALITY OF NONVERBAL COMMUNICATION RADIOS

(71) Applicant: Battelle Memorial Institute, Columbus, OH (US)

(72) Inventors: Samuel Colachis, Columbus, OH (US); Eric Meyers, Columbus, OH (US); Justin Sanchez, Vienna, VA (US); David Friedenberg, Worthington, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 17/336,556

(22) Filed: Jun. 2, 2021

(65) Prior Publication Data
US 2021/0382554 A1    Dec. 9, 2021

Related U.S. Application Data

(60) Provisional application No. 63/072,552, filed on Aug. 31, 2020, provisional application No. 63/035,709, filed on Jun. 6, 2020.

(51) Int. Cl.
*A61N 1/36* (2006.01)
*G06F 3/01* (2006.01)
(Continued)

(52) U.S. Cl.
CPC ........... *G06F 3/015* (2013.01); *A61N 1/0484* (2013.01); *A61N 1/36031* (2017.08);
(Continued)

(58) Field of Classification Search
CPC .... G06F 3/015; G06N 20/00; A61N 1/36031; A61N 1/0484; A61N 1/36034; G16H 40/67; G16H 80/00
See application file for complete search history.

(56) References Cited

U.S. PATENT DOCUMENTS 9,257,133 B1 *  2/2016  Strand ................... G06N 20/00
9,314,190 B1 *  4/2016  Giuffrida ............. A61B 5/4082
(Continued)

FOREIGN PATENT DOCUMENTS

EP    0857396 A1    8/1998
EP    1780625 A1    5/2007

OTHER PUBLICATIONS

Bouton et al., "Restoring cortical control of functional movement in a human with quadriplegia", Nature 533, 247 250, doi:10.1038/nature17435 (2016).
(Continued)

*Primary Examiner* — Amanda K Hulbert
*Assistant Examiner* — Natasha Patel
(74) *Attorney, Agent, or Firm* — Fay Sharpe LLP

(57) ABSTRACT

A communications radio includes an array of electrodes configured to be disposed on a body part, a radio transceiver, an electrical stimulation transmitter, electromyography (EMG) receive circuitry, and a data processing sub-module which configured to perform radio communication. The communication includes, using the electrical stimulation transmitter and the array of electrodes, presenting semantic messages received via the radio transceiver as electrical stimulation patterns. The communication further includes, via the radio transmitter, transmitting semantic messages determined from EMG signals measured using the array of electrodes and the EMG receive circuitry. The communications radio may further include a garment wearable on the
(Continued)

body part with the array of electrodes in electrical contact with skin of the body part.

16 Claims, 5 Drawing Sheets

(51) Int. Cl.
*G16H 40/67* (2018.01)
*G16H 80/00* (2018.01)
*G06N 20/00* (2019.01)
*A61N 1/04* (2006.01)

(52) U.S. Cl.
CPC ......... *A61N 1/36034* (2017.08); *G06N 20/00* (2019.01); *G16H 40/67* (2018.01); *G16H 80/00* (2018.01)

(56) References Cited

U.S. PATENT DOCUMENTS

| | | | |
|---|---|---|---|
| 2004/0122707 A1* | 6/2004 | Sabol | G07C 9/37 705/2 |
| 2010/0134327 A1 | 6/2010 | Dinh et al. | |
| 2012/0188158 A1 | 7/2012 | Tan et al. | |
| 2014/0240103 A1 | 8/2014 | Lake et al. | |
| 2015/0177835 A1 | 6/2015 | Gazetta | |
| 2015/0306373 A1 | 10/2015 | Bouton | |
| 2016/0313801 A1 | 10/2016 | Wagner et al. | |
| 2018/0036531 A1* | 2/2018 | Schwarz | A61N 1/0484 |
| 2018/0154132 A1 | 6/2018 | Bouton | |
| 2018/0154133 A1 | 6/2018 | Bouton | |
| 2018/0154140 A1 | 6/2018 | Bouton | |
| 2018/0301060 A1 | 10/2018 | Israr et al. | |
| 2018/0307313 A1 | 10/2018 | Belomoev | |
| 2019/0224473 A1 | 7/2019 | Bouton | |
| 2020/0206503 A1 | 7/2020 | Ganzer | |
| 2020/0276438 A1 | 9/2020 | Bouton | |
| 2020/0405188 A1 | 12/2020 | Sharma | |
| 2020/0406035 A1 | 12/2020 | Sharma | |
| 2021/0038887 A1 | 2/2021 | Bouton | |

OTHER PUBLICATIONS

Colachis et al., "Dexterous Control of Seven Functional Hand Movements Using Cortically-Controlled Transcutaneous Muscle Stimulation in a Person With Tetraplegia", Front Neurosci 12, 208, doi:10.3389/fnins.2018.00208 (2018).

Fredenberg et al., "Neuroprosthetic-enabled control of graded arm muscle contraction in a paralyzed human", Scientific Reports 7 (2017).

Sharma et al., "Using an Artificial Neural Bypass to Restore Cortical Control of Rhythmic Movements in a Human with Quadriplegia", Sci Rep 6, 33807, doi:10.1038/srep33807 (2016).

Skomrock et al., "A Characterization of Brain-Computer Interface Performance Trade-Offs Using Support Vector Machines and Deep Neural Networks to Decode Movement Intent", Front Neurosci 12, 763, doi:10.3389/fnins.2018.00763 (2018).

Schwemmer et al., "Meeting brain-computer interface user performance expectations using a deep neural network decoding framework", Nature Medicine 24, 1669-1676, doi:10.1038/s41591-018-0171-y (2018).

Ren et al., Intramuscular EMG Decomposition Basing on Motor Unit Action Potentials Detection and Superposition Resolution. Front Neurol 9, 2, doi: 10.3389/fneur.2018.00002 (2018).

Farina et al., "Principles of Motor Unit Physiology Evolve With Advances in Technology", Physiology (Bethesda) 31, 83-94, doi:10. 1152/physiol.00040.2015 (2016).

Bockbrader et al., "Clinically Significant Gains in Skillful Grasp Coordination by an Individual With Tetraplegia Using an Implanted Brain-Computer Interface With Forearm Transcutaneous Muscle Stimulation", Arch Phys Med Rehabil 100, 1201-1217, doi:10.1016/j.apmr.2018.07.445 (2019).

Storn et al., "Differential evolution-a simple and efficient heuristic for global optimization over continuous spaces", Journal of global optimization 11, 341-359 (1997)).

Zuzheng, Lou et al, Wireless Master-Slave FES Rehabilitation System Using sEMG Control, Intelligent Robotics and Applications, Springer Berlin Heidelberg, Berlin, Heidelberg, pp. 1-10 Figure 1.

* cited by examiner

NON-VERBAL COMMUNICATIONS RADIO AND NON-VERBAL COMMUNICATION SYSTEM USING A PLURALITY OF NONVERBAL COMMUNICATION RADIOS

This application claims the benefit of U.S. Provisional Application No. 63/035,709 filed Jun. 6, 2020 and titled "NON-VERBAL COMMUNICATIONS RADIO AND NON-VERBAL COMMUNICATION SYSTEM USING A PLURALITY OF NON-VERBAL COMMUNICATION RADIOS". This application claims the benefit of U.S. Provisional Application No. 63/072,552 filed Aug. 31, 2020 and titled "NON-VERBAL COMMUNICATIONS RADIO AND NON-VERBAL COMMUNICATION SYSTEM USING A PLURALITY OF NON-VERBAL COMMUNICATION RADIOS".

U.S. Provisional Application No. 63/035,709 filed Jun. 6, 2020 and titled "NON-VERBAL COMMUNICATIONS RADIO AND NON-VERBAL COMMUNICATION SYSTEM USING A PLURALITY OF NON-VERBAL COMMUNICATION RADIOS" is incorporated herein by reference in its entirety.

U.S. Provisional Application No. 63/072,552 filed Aug. 31, 2020 and titled "NON-VERBAL COMMUNICATIONS RADIO AND NON-VERBAL COMMUNICATION SYSTEM USING A PLURALITY OF NON-VERBAL COMMUNICATION RADIOS" is incorporated herein by reference in its entirety.

BACKGROUND

The following relates to the radio communication system arts, non-verbal communication device and method arts, and to like applications.

Radio communication systems are ubiquitous in the modern world. Many police and military organizations employ radios working on secure radio frequency (RF) channels for covert communications. Sports teams such as the National Football League (NFL) employ radios for communication between the coach and quarterback. Miniaturized radios particularly enable mobile personnel such as police officers, NFL quarterbacks, and the like to maintain radio communications with headquarters, coaching staff, etc. Such a radio typically includes a microphone via which the radio user sends messages, and a headset or loudspeaker via which the radio receives messages.

Certain improvements are disclosed herein.

BRIEF SUMMARY

In accordance with some illustrative embodiments disclosed herein, a communications radio is disclosed, comprising: an array of electrodes configured to be disposed on a body part; a radio transceiver; an electrical stimulation transmitter operatively coupled with the array of electrodes; electromyography (EMG) receive circuitry operatively coupled with the array of electrodes; and a data processing sub-module configured to perform radio communication including (i) using the electrical stimulation transmitter and the array of electrodes, presenting semantic messages received via the radio transceiver as electrical stimulation patterns, and (ii) via the radio transmitter, transmitting semantic messages determined from EMG signals measured using the array of electrodes and the EMG receive circuitry.

In accordance with some illustrative embodiments disclosed herein, the data processing sub-module of the communications radio of the immediately preceding paragraph includes an electronic processor and a non-transitory storage medium storing instructions readable and executable by the electronic processor to: (i) receive a radio signal via the radio transceiver, determine a semantic message from the received radio signal, encode an electrical stimulation pattern representing the semantic message determined from the received radio signal, and apply the electrical stimulation pattern using the electrical stimulation transmitter and the array of electrodes, and to (ii) receive EMG signals via the array of electrodes and the EMG receive circuitry, determine a semantic message from the EMG signals, encode a radio signal representing the semantic message determined from the EMG signals, and transmit the encoded radio signal via the radio transceiver. In some such embodiments, the non-transitory storage medium further stores a semantic database containing: information for determining the semantic message from the received radio signal and for encoding the electrical stimulation pattern representing the semantic message determined from the received radio signal, and information for determining the semantic message from the EMG signals. The information for determining the semantic message from the received radio signal comprises at least one look-up table that associates radio signals with corresponding semantic messages. The information for encoding the electrical stimulation pattern representing the semantic message determined from the received radio signal comprises at least one look-up table that associates semantic messages with corresponding spatiotemporal electrical stimulation patterns. The information for determining the semantic message from the EMG signals comprises parameters of an EMG decoder implemented as a machine learning component trained to translate received EMG signals into corresponding semantic messages.

In accordance with some illustrative embodiments disclosed herein, the data processing sub-module of the communications radio of either of the two immediately preceding paragraphs is configured to perform time domain multiplexing in which: (i) during a receive time interval the electrical stimulation transmitter is operatively connected to the array of electrodes to present semantic messages received via the radio transceiver as electrical stimulation patterns, and (ii) during a transmit time interval the EMG receive circuitry is operatively connected to the array of electrodes to transmit semantic messages determined from EMG signals measured using the array of electrodes and the EMG receive circuitry. In some such embodiments, the communications radio further comprises an EMG/electrical stimulation switch operative to (i) switch to connect the EMG receive circuitry to the array of electrodes and simultaneously isolate the electrical stimulation transmitter from the array of electrodes, and (ii) switch to connect the electrical stimulation transmitter to the array of electrodes and simultaneously isolate the EMG receive circuitry from the array of electrodes.

In accordance with some illustrative embodiments disclosed herein, a communications radio of any of the three immediately preceding paragraphs further comprises a garment wearable on a body part with the array of electrodes in electrical contact with skin of the body part. In some such embodiments, the garment comprises at least one of a sleeve and/or a legging.

In accordance with some illustrative embodiments disclosed herein, a radio communications method comprises: presenting a received semantic message, and sending an outgoing semantic message. The presenting of the received semantic message is by operations including receiving a radio signal using a radio transceiver, determining the received semantic message from the received radio signal, and applying an electrical stimulation pattern to a body part wherein the electrical stimulation pattern represents the semantic message determined from the received radio signal. The sending of the outgoing semantic message is by operations including receiving EMG signals, determining the outgoing semantic message from the EMG signals, and transmitting the outgoing semantic message as a radio signal encoding the outgoing semantic message and transmitted using the radio transceiver.

In accordance with some illustrative embodiments disclosed herein, a communications radio comprises: an array of electrodes configured to be disposed on a body part; a radio receiver; an electrical stimulation transmitter operatively coupled with the array of electrodes; and a data processing sub-module configured to perform radio communication including, using the electrical stimulation transmitter and the array of electrodes, presenting semantic messages received via the radio receiver as electrical stimulation patterns.

In accordance with some illustrative embodiments disclosed herein, a communications radio comprises: an array of electrodes configured to be disposed on a body part; a radio transmitter; electromyography (EMG) receive circuitry operatively coupled with the array of electrodes; and a data processing sub-module configured to perform radio communication including, via the radio transmitter, transmitting semantic messages determined from EMG signals measured using the array of electrodes and the EMG receive circuitry.

In accordance with some illustrative embodiments disclosed herein, a remote three dimensional (3D) electrical impedance tomography (EIT) imaging device comprises an array of electrodes, a garment wearable on a body part with the array of electrodes in electrical contact with skin of the body part, a radio transmitter, and an electronics module. The electronics module is configured to acquire 3D EIT imaging data using the array of electrodes and to transmit the acquired 3D EIT imaging data using the radio transmitter.

In accordance with some illustrative embodiments disclosed herein, a training device comprises an array of electrodes, a garment wearable on a body part with the array of electrodes in electrical contact with skin of the body part, and an electronics module. The electronics module is configured to use the array of electrodes of the learner wearable device to apply a somatosensation pattern providing guidance in performing a motor action, such as (by way of non-limiting illustrative example) a gaming controller action, a motor action performed during sports activity, a motor action performed to play a musical instrument. Optionally, the electronics module of the learner wearable device is further configured to measure electromyography (EMG) signals generated by the wearer of the learner wearable device using the array of electrodes of the learner wearable device, and the application of the somatosensation pattern providing guidance in performing the motor action is controlled at least in part by the measured EMG signals. In some embodiments, an expert wearable device is also provided, in which the electronics module of the expert wearable device is configured to use the array of electrodes of the expert wearable device to acquire the somatosensation pattern from a wearer of the expert wearable device while the expert is performing the motor action.

In accordance with some illustrative embodiments disclosed herein, a medical diagnostic device comprises an array of electrodes, a garment wearable on a body part with the array of electrodes in electrical contact with skin of the body part, and an electronics module. The electronics module is configured to use the array of electrodes of the patient wearable device to apply different pain somatosensation patterns sequentially to a wearer of the patient wearable device. In some embodiments, the medical diagnostic device further includes an analogous physician wearable device, and the patient wearable device and the physician wearable device are in communication so as to apply the same somatosensation pattern at the same time using both the patient wearable device and the physician wearable device. In some embodiments, the medical diagnostic device further comprises a non-transitory storage medium storing a library of annotated pain somatosensations each being annotated with a corresponding pathology or pathologies that produce the type and level of pain represented by the annotated pain somatosensation, and the different pain somatosensation patterns applied sequentially to a wearer of the patient wearable device are retrieved from the library of annotated pain somatosensations.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

Figure 1:
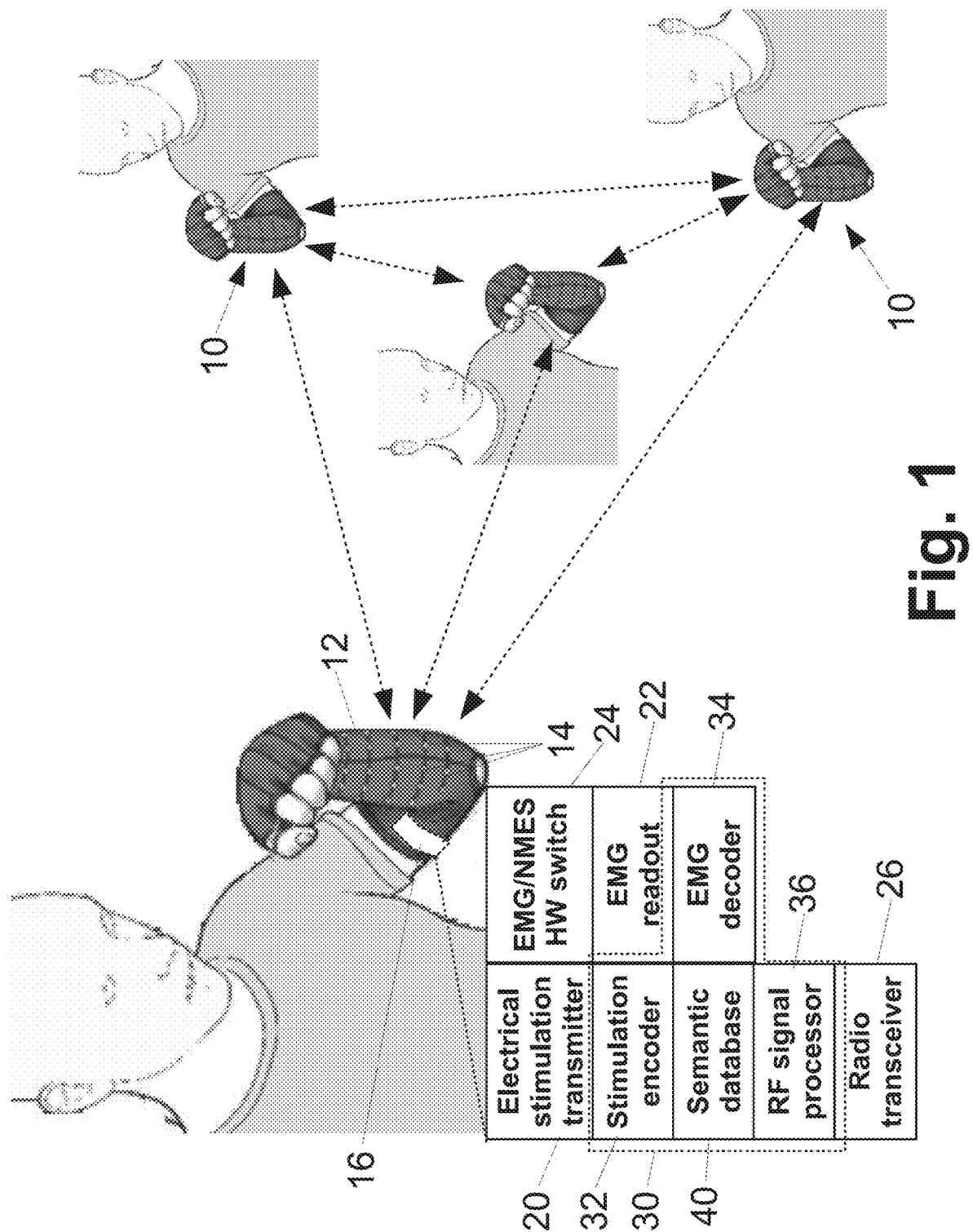
FIG. 1 diagrammatically illustrates a non-verbal communications system.

As noted, miniaturized radios enable mobile personnel such as police officers, military team members, NFL quarterbacks, and the like to maintain radio communications with headquarters, coaching staff, other team members, or so forth. However, problems can arise. While a secure RF channel may be used to mitigate or eliminate concerns about electronic eavesdropping on the radio transmissions, at the transmitting/receiving end the radio transmissions are usually converted by transducers (microphones, loudspeakers) to/from voice/audio. These audio signals can more easily be picked up by an eavesdropper, for example using a directional microphone. Mobile personnel also sometimes operate in noisy environments such as a battlefield or sports stadium, so that ambient audio noise can interfere with conveying information verbally. Furthermore, some mobile personnel operate in environments in which speaking or listening to audio messages can introduce safety concerns. For example, a member of a military force deployed in hostile territory may give away his or her location by speaking and listening to radio communications. Use of headphones for receiving radio messages, and a throat microphone or laryngophone for transmitting messages, can reduce likelihood of radio usage giving away location.

However, headphones can reduce environmental awareness by blocking ambient sounds, and throat microphones can produce weak audio and may still present sufficient noise to give away a position.

A further difficulty is that in some situations, verbal communications may be difficult or impossible. For example, a soldier, police officer, or football player engaged in strenuous running may find it difficult or impossible to verbalize messages. The content of some messages that might be useful to convey, such as excessive fatigue of a military team member or football player, may not be obvious to the fatigued person due to the adrenaline rush caused by engagement in a dangerous and/or strenuous activity.

Moreover, radio systems that rely upon audio/voice communications are limited in the types and efficiency of information communicated. Attempting to convey complex information such as informing other military unit members that a certain member is injured can be difficult, requiring verbal articulation of the situation (injury) and the person in that situation. Verbal communications are also inefficient for tasks such as controlling robotic assets such as an unmanned aerial vehicle (UAV). Navigational information can also be difficult to clearly convey via verbal/audio, especially in scenarios where closely coordinated movements are essential, such as members of a military team attempting simultaneously engage a specific target. Likewise, in a football play, attempting to coordinate between a receiver running a pass route and a quarterback (who may be scrambling out of the pocket) is difficult to do verbally. Efficiency in communication is especially important in tasks such as military operations, high-risk police actions such civil disturbance control, and football plays, where the mobile personnel need to receive timely information while maintaining constant situational awareness of myriad environmental inputs such as recognizing sounds and sights, and while maintaining a mental picture of relevant information such as the deployment of team members. In such environments, the acts of listening to radio transmissions and converting the received verbal messages into actionable intelligence can distract from other aspects of optimal performance.

In embodiments disclosed herein, a non-verbal communication radio includes a wearable garment with an embedded high-density array of electrodes is worn by mobile personnel. The radio further includes a radio transceiver, and electronics configured to provide message transmission and reception. To implement message transmission, the electronics are configured to: measure electromyography (EMG) generated by muscles and measured by the electrodes of the wearable garment; decode measured EMG signals determine semantic messages; encode the semantic messages are radio signals; and control the radio transceiver to transmit the radio signals representing the semantic messages. To implement message reception, the electronics are configured to: receive radio signals representing semantic messages (which are generated by another non-verbal communications radio), decode/process the radio signals to determine the semantic messages; encode the semantic messages as electrical stimulation patterns; and apply the electrical stimulation patterns by energizing the electrodes of the wearable garment.

With reference to FIG. 1, a communication system including a plurality of such non-verbal communication radios 10 is diagrammatically illustrated. Each non-verbal communication radio 10 is worn by an individual, who may for example be a member of a military unit, or a player on a football team, or a police officer of a policing unit engaging a civil disturbance, or so forth. Each of the non-verbal communication radios 10 is substantially similar, and so, features of the radios 10 are labeled and diagrammatically shown in additional detail in only one of the non-verbal communication radios 10 at the left-hand side of FIG. 1. The non-verbal communication radio 10 includes a wearable garment 12 with electrodes 14 arranged facing the skin so as to contact the skin. (Note that while the electrodes are visible in FIG. 1 for illustration, in some embodiments the electrodes are inside the garment 12 and hence are not visible from the outside). The electrodes include suitable contacts such as hydrogel contacts. For embodiments in which high energy electrical stimulation is to be applied, the hydrogel contacts may optionally comprise sheets extending between the electrodes.

Such wearable garments with electrodes are known for use in electro-neural therapies for medical patients such as stroke victims, patients who are partially or wholly paralyzed due to a spinal cord injury, and so forth. Some suitable embodiments of the garment 12 with electrodes 14 are described, by way of non-limiting illustrative example, in Bouton et al., U.S. Pub. No. 2018/0154133 A1 published Jun. 7, 2018 which is in incorporated herein by reference in its entirety and in Bouton et al., U.S. Pub. No. 2018/0154140 A1 published Jun. 7, 2018 which is in incorporated herein by reference in its entirety and in Bartholomew et al., U.S. Pub. No. 2018/0001086 A1 published Jan. 4, 2018 which is in incorporated herein by reference in its entirety and in Bouton et al., U.S. Pub. No. 2015/0306373 A1 published Oct. 29, 2015 which is in incorporated herein by reference in its entirety.

In the illustrative examples, the wearable garment 12 is a wearable sleeve that is worn on the arm of the mobile person, as illustrated. However, more generally, the wearable garment may be a legging that is worn on the leg of the mobile person, or a wearable vest or chest band that is worn on the torso and/or abdomen of the mobile person, and/or so forth. Moreover, while use of the wearable garment 12 is beneficial as it provides an efficient way to place a large and dense array of electrodes 14 over an extended area of skin, in some embodiments the array of electrodes 14 may be placed on the skin without the use of a garment serving as a support or substrate for the electrodes 14. For a large array of electrodes, this could be tedious as each electrode would need to be individually placed. If the garment 12 is employed, the placement can be done quickly, simply by putting the garment on. In some embodiments, the garment 12 could take the form of a garment of a type not typically used in clothing persons. For example, the garment 12 carrying the electrodes 14 could be an adhesive tape that is wrapped around the arm of the wearer.

The non-verbal communication radio 10 further includes an electronics module 16, which may be embedded in the wearable garment 12 (as diagrammatically shown) or may be separate from the wearable garment and connected with the electrodes of the garment by suitable wiring. (As an example of the latter, the electronics module 16 could alternatively be embodied as an armband). The electronics module 16 may, for example, comprise electronic mounted on one or more small printed-circuit boards, or on a single flexible printed circuit board, or some combination of these arrangements, or so forth.

The illustrative electronics module 16 includes an electrical stimulation transmitter 20 for transmitting electrical stimulation pulses to selected electrodes 14 and electromyography (EMG) readout circuitry 22 for reading EMG signals from the electrodes. The electrical stimulation transmitter 20 typically includes a multichannel simulator allowing for applying electrical stimulation signals with programmed parameters (e.g. amplitude, frequency, waveform, etcetera) to specific electrodes or groups of electrodes. Depending on the magnitude and other characteristics of the stimulation, it may induce functional electrical stimulation (FES) in which muscles are caused to contract by application of the electrical stimulation; or it may induce somatosensations such as a haptic response. The EMG readout circuitry 22 typically includes preamplifiers for amplifying the low-strength EMG signals and analog-to-digital (A/D) converters for digitizing the amplified EMG signals. The EMG readout circuitry 22 is preferably multichannel so that measured EMG signals are associated to specific electrodes or groups of electrodes. Furthermore, to enable use of the same electrodes 14 for both EMG readout and electrical stimulation, the illustrative electronics module 16 further includes an EMG/electrical stimulation hardware (HW) switch 24 (e.g., a solid state relay such as a high voltage MOSFET or power transistor) that (1) isolates the EMG readout circuitry 22 from the electrodes 14 and connects the electrical stimulation transmitter 20 during the electrical stimulation phase; and (2) isolates the electrical stimulation transmitter 20 from the electrodes 14 and connects the EMG readout circuitry 22 during the EMG readout phase. Other approaches for implementing both electrical stimulation and EMG readout with the same electrodes are also contemplated, such as use of optoisolators. In another contemplated approach, separate sets of electrodes are used for electrical stimulation and EMG. (In this case, there still may be benefit to time-domain multiplexing between the electrical stimulation and EMG, since electrical stimulation signals applied during EMG readout would likely interfere with the EMG signal quality).

As further illustrated in FIG. 1, the illustrative electronics module 16 further includes a radio transceiver 26, which transmits and receives radio signals. The choice of radio frequency (RF) channel, modulation scheme, optional encryption, and so forth is application-specific. For example, if the disclosed non-verbal communication system is deployed by a military force then strong encryption is suitable, and the RF channel is suitably one allocated for use by the military force. If the disclosed non-verbal communication system is deployed by a police force then strong encryption is again suitable, and the RF channel is suitably one allocated for use by the police force. If the disclosed non-verbal communication system is deployed by a sports team during a game then encryption may or may not be employed, and the RF channel is suitably one allocated for use by the sports team or by civilians generally. The range of the radio transceiver 26 is also suitably chosen based on the application. For use by a football team, for example, the range may only need to be around 150-200 yards, given that a football field (excluding end zones and sideline area) is 100 yards in length. On the other hand, for use by a military force a longer range may be needed, based on the credibly expected area of deployment and operations. It is also noted that the radio transceiver 26 may be chosen to operate on any suitable frequency band of the electromagnetic spectrum, and is not limited to conventional "radio bands". For example, the radio transceiver 26 may operate in a MHz band, a GHz band, or so forth.

Furthermore, it is contemplated for the radio transceiver 26 to be embodied as a single radio transceiver o having both transmit and receive capability; or as separate radio receiver and radio transmitter components that together form the radio transceiver 26. Moreover, in some embodiments the non-verbal communication radio 10 may be a one-way radio including only transmit capability (but not receive capability). In this case the switch 24, electrical stimulation transmitter 20 and electrical stimulation encoder 32 are suitably omitted, and the radio transceiver 26 is suitably replaced by a radio transmitter having with no receive capability. Conversely, in some embodiments the non-verbal communication radio 10 may be a one-way radio including only receive capability (but not transmit capability). In this case the switch 24, EMG readout circuitry 22, and EMG decoder 34 are suitably omitted, and the radio transceiver 26 is suitably replaced by a radio receiver having with no transmit capability.

As further illustrated in FIG. 1, the illustrative electronics module 16 further includes a data processing sub-module 30 which typically includes an electronic processor (e.g. microprocessor or microcontroller) and non-transitory storage medium (details not shown). The electronic processor is preferably a low power microprocessor or microcontroller of a type used in cellular telephones or other mobile devices. The non-transitory data storage may, for example, comprise a flash memory, read-only memory (ROM), or other electronic memory (or additionally or alternatively, an optical or magnetic memory such as a miniature hard disk or optical disk). The electronic processor reads and executes instructions stored on the non-transitory storage medium to perform data processing functions as disclosed herein, such as diagrammatically indicated electrical stimulation encoder 32, EMG decoder 34, and RF signal processor 36.

The non-transitory storage medium of the data processing sub-module 30 further stores a semantic database 40 which contains information for interpreting EMG signals output by the EMG readout circuitry 22 into semantic messages generated by the wearer of the non-verbal communication radio 10. For example, the semantic messages may include: commands intended to be sent to other mobile personnel; control commands intended to be sent to a UAV or other device; informational messages such as reporting on the status of the wearer; and so forth. It is to be appreciated that the semantic messages may or may not be volitionally generated by the wearer. For example, while a semantic message indicating a command to "advance" sent to the other mobile personnel may be volitionally generated, a semantic message indicating excessive fatigue of the wearer may be generated in a non-volitional manner, e.g. based on the EMG measurements indicating fatigue of the wearer.

The information for interpreting the EMG signals may be suitably stored as parameters of an EMG decoder implemented as an artificial neural network (ANN), support vector machine (SVM), or other machine learning (ML) component trained to translate received EMG signals into corresponding semantic messages. Such training is typically done offline and for a specific wearer (given that EMG signals are often strongly individualistic), for example by having the wearer perform movements corresponding to the intended semantic message (e.g. hand clench to indicate "hold position", holding a specific two fingers out to indicate "move forward", or so forth) while measuring the EMG signals and then performing supervised training of the ML component using this collected EMG data to optimally train the ML component to output the correct intended semantic message in response to receiving the corresponding EMG signals.

Similarly, the semantic database 40 stored on the non-transitory storage medium contains information for interpreting radio signals received via the radio transceiver 26 into semantic messages that are translated into a spatiotemporal electrical stimulation patterns that is then applied to the skin of the wearer by the electrical stimulation transmitter 20. For example, the semantic database 40 may store look-up tables that associate certain radio signals with corresponding semantic messages, and may store look-up tables associating the semantic messages with corresponding spatiotemporal electrical stimulation patterns that represent those semantic messages.

In addition to the foregoing components, the non-verbal communication radio 10 may further include additional components for specific situations. For example, the non-verbal communication radio 10 may optionally include a conventional microphone and (e.g. Bluetooth) headset to enable the wearer to transmit and receive conventional verbal communications when such communication is effective (e.g., prior to the military force entering the combat zone, or during parts of a football game in which crowd noise is not so loud as to block verbal communication). Other sensors may be included in the wearable garment, such body temperature sensors, heart rate sensors, accelerometers or other inertial measurement units (IMUs), and so forth, and the EMG decoder 34 may then be expanded to also decode semantic messages based on these further inputs (e.g. body temperature, heart rate, motion measured by the accelerometer, et cetera). If an IMU is provided on the arm, this can be used to measure the arm orientation, which in turn can improve performance accuracy of the EMG decoder 34 by having the accelerometer reading as an additional input to the EMG decoder 34. As another example, while in some embodiments the electronics module 16 may include an on-board battery (not shown) for providing power to the various components, if additional power is needed then a belt-worn battery (not shown) may be connected with the non-verbal communication radio 10 via a suitable power cable. In another variant embodiment, the wearable garment containing the electrodes may comprise two or more garments, e.g. a left-arm sleeve, a right-arm sleeve, a left-leg legging, and a right-leg legging. In such an embodiment, a further short-range radio (e.g. Bluetooth) may be incorporated into each garment in order to allow intercommunication between the various garments (e.g. the left and right sleeves and the left and right leggings) to enable them to operate as a single functional unit. In such an arrangement, only one of these garments may include the electronics module 16, or as previously noted the electronics module 16 may be embodied as a separate component, e.g. a belt-worn module, that is connected with the various garments.

In another contemplated variant, the information contained in the semantic database 40 stored on the non-transitory storage medium of the data processing sub-module 30 of the electronics module 16 may optionally include addressing information for enabling targeted messaging between specific members (or groups of members) of the military, police, or sports team employing the non-verbal communication system. Such addressing information enables a wearer to send a targeted semantic message to a specific member (or group of members) of the military, police, sports, or other team. Various approaches can be used. For example, if the team consists of fewer than five members (or ten members if the garment includes left and right sleeves), then the wearer may use a specific finger to articulate a movement conveying a message, with the finger used corresponding to the specific other team member that is the target of the message. In this embodiment, sending the message to two or more members would merely involve making the same finger movement simultaneously with the corresponding two or more fingers. This is merely an illustrative example. In a similar variant, specific semantic messages may be automatically targeted to specific individuals. For example, a message indicating a receiver should shadow the scrambling quarterback (in a football example) might only be sent to the team members who are receivers. In a variant, the same EMG signals generated by the quarterback (perhaps non-volitionally, e.g. by the EMG readout circuitry detecting rapid movement by the quarterback) may be output as different messages for different team members (e.g., a "shadow quarterback" message sent to the team's receivers, and a different message sent to the team's linesmen to coordinate a modified formation for protecting the scrambling quarterback). These are again merely examples.

Preferably, the electrodes 14 from a high-density array suitable for measuring high-density electromyography (HDEMG), and suitable for applying complex spatiotemporal electrical stimulation patterns to the wearer's skin. For example, in some embodiments in which the garment 12 is a sleeve (as illustrated), the sleeve 12 may have 130-160 electrodes, although more or fewer electrodes are also contemplated. For electrical stimulation intended to generate somatosensations but not functional electrical stimulation (FES), a higher density of electrodes may be feasible due to the lower electrical stimulation amplitudes typically applied to generate somatosensations, as compared with FES where voltages on the order of 100-200 volts or more may be applied.

Figure 2:
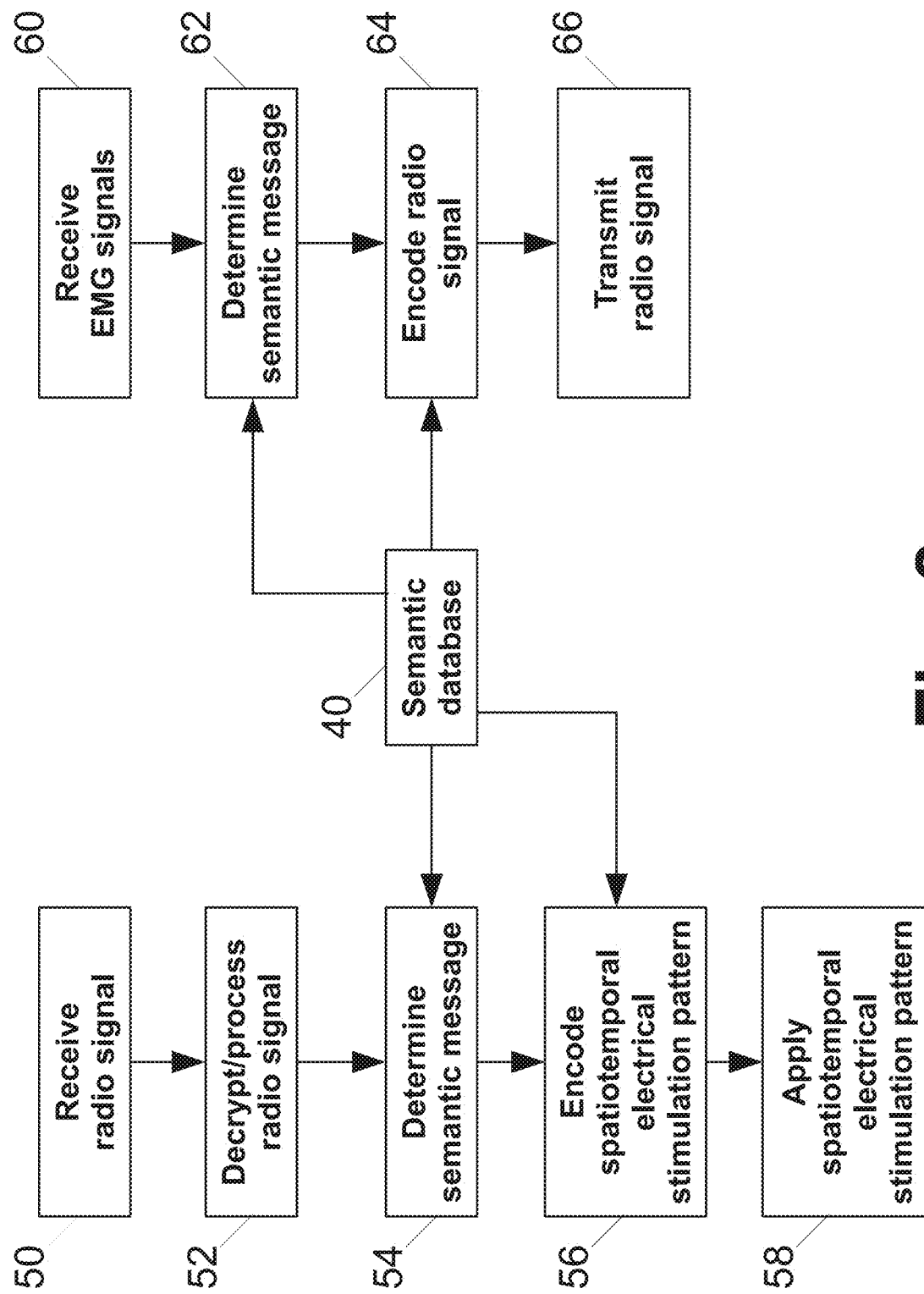
FIG. 2 diagrammatically shows processing for sending and receiving semantic messages using a non-verbal communication radio of the system of FIG. 1.

With reference now to FIG. 2, an illustrative usage of the non-verbal communication radio 10 is described. The left-hand flow chart of FIG. 2 depicts a processing sequence by which a semantic message is received via the radio transceiver 26 and conveyed to the wearer as a spatiotemporal electrical stimulation pattern. The right-hand flow chart of FIG. 2 depicts a processing sequence by which the wearer generates a semantic message by EMG signals and transmits the semantic message via the radio transceiver 26.

Starting with the receive processing (left-hand flow chart of FIG. 2), at an operation 50 a radio transmission is received via the radio transceiver 26. At an optional operation 52 the radio transmission is decoded or processed by the RF signal processor 36 of FIG. 1. This optional operation 52 may include operations such as decrypting the radio transmission, filtering the radio transmission, performing analog-to-digital (ND) conversion, and/or so forth. In an operation 54 performed by the electrical stimulation encoder 32, the semantic message conveyed by the radio transmission is determined with reference to the semantic database 40. For example, various (decoded/filtered) radio signals may be associated to specific semantic messages by way of a look-up table. Optionally, the operation 54 may also include determining to whom the radio transmission is addressed. In general, the radio transceiver 26 is (at least approximately) omnidirectional (as opposed to being, for example, a narrow beam transmission), and so a radio message is transmitted to all members of the police, military, or sports team having one of the non-verbal communication radios 10 (excepting the sender of the message). If the semantic message carried by the radio transmission includes address information then this is decoded as part of the operation 54. To this end, the semantic database 40 includes the addresses of the wearer and other members of the team. The addresses can be any identifier number, string, or other representation that uniquely identifies specific users. In some variants, groups of users may be similarly identified by group membership information contained in the semantic database 40. If it is determined that the wearer is not an intended recipient of the message then it is discarded and not further acted upon.

In an operation 56 further suitably performed by the electrical stimulation encoder 32, a spatiotemporal electrical stimulation pattern is encoded that represents the determined semantic message. At an operation 58 the spatiotemporal pattern is applied by way of the electrical stimulation transmitter 20 and electrodes 14. The operation 56 may be viewed as a language translation operation, in which the semantic message determined at the operation 54 is translated into a spatiotemporal electrical stimulation pattern that represents the semantic message. This is done by a translation table or other translation information contained in the semantic database 40. The spatiotemporal electrical stimulation pattern may have spatial variation, or may have temporal variation, or may have both spatial and temporal variation. By way of some illustrations, the spatiotemporal electrical stimulation pattern might be an electrical stimulation pattern that produces a haptic sensation on a particular area of the arm; or might be an electrical stimulation pattern that varies over time, e.g. being sensed as three taps to the wearer's arm; or might be an electrical stimulation pattern that produces a sensation of a touch that moves across the arm over some time interval. It will be appreciated that the wearer of the non-verbal communications radio 10 must be trained (i.e. informed) prior to using the radio 10 to recognize the semantic message that is conveyed by the spatiotemporal pattern. For example, the wearer may have been trained to recognize the sensation of a touch that moves across the arm over some time interval to convey the message "advance forward". As another example, a receiver in a football game may be trained to recognize three taps to the arm as conveying the message that the quarterback is now scrambling out of the pocket. In some embodiments, the applied spatiotemporal electrical stimulation pattern may be sufficient to actually evoke contraction of the muscles to which the electrical stimulation is applied—in this case the spatiotemporal electrical stimulation pattern produces functional electrical stimulation (FES). In some embodiments, the applied spatiotemporal electrical stimulation pattern may be effective to paralyze the affected muscles. This could be useful, for example, if the intended message is that the recipient should not fire his or her rifle—the electrical stimulation pattern may therefore paralyze the trigger finger, both producing a sensation comprehensible by the recipient and also actively preventing the action of firing the rifle. These are merely non-limiting illustrative examples.

Next, addressing the transmit processing (right-hand flow chart of FIG. 2), at an operation 60 the EMG readout circuitry 22 (see FIG. 1) receives EMG signals from the electrodes 14. In an operation 62, the semantic message intended to be conveyed by the EMG signals is determined by decoding the EMG signals using the EMG decoder 34. This is suitably done by applying an ANN, SVM, or other ML component to the measured EMG signals, using pre-trained parameters stored in the semantic database 40. This operation 62 may also be viewed as a language translation operation, in which the EMG signals measured at the operation 60 are translated into a semantic message. For example, moving the index finger from an upward position to a horizontal position may represent the semantic message "advance forward". The wearer is presumed to have been pre-trained to use this motion to indicate "advance forward". In some embodiments, it may be sufficient for the wearer to intend the movement without actually actuating movement of the hand, arm, or other body part. This is because EMG signals may be generated in such a situation. As a further example, the received EMG signals may not necessarily have been volitionally generated. That is, the wearer may not have actually intended to produce the received EMG signals. For example, a wearer who is excessively fatigued may produce involuntary muscle tremors with corresponding EMG signals that are detected in the operation 60 and determined in the operation 62 to convey a semantic message of excessive fatigue. Furthermore, the EMG signals may indicate intended recipient address information, e.g. if there are five members of a team then the wearer may direct a message to a particular member based on which finger is moved to generate the EMG signal detected at the operation 60.

In an operation 64 performed by the RF signal processor 36, the determined semantic message is encoded into a radio signal. This encoding can use any parameter or parameters of the radio signal to encode the semantic message. For example, the semantic message may be encoded as a radio signal using a type of phase shift keying (PSK), a type of quadrature phase shift keying (QPSK), binary phase shift keying (BPSK), or so forth. If the number of semantic messages that are intended to be conveyed is a small set, then a simpler radio signal encoding can be used, e.g. sending on different pre-designated analog frequencies indicating different respective semantic messages. Optionally, in the operation 64 the radio signal may be encrypted or otherwise processed, analogously to the operation 52 of the message receive chain. Optionally, in some embodiments the operation 64 may add address information to the encoded radio signal. For example, certain messages may only be intended to go to a particular person (e.g., the quarterback, or a military group leader) or a particular group of persons (e.g., all receivers on a football team), and in this case the address information can be added at the operation 64. These are merely some non-limiting illustrative examples. In an operation 66, the radio signal is transmitted by the radio transceiver 26.

Typically, it is not practical to perform the receive processing and the transmit processing shown in FIG. 2 simultaneously. This is because the applied electrical stimulation can stimulate muscles to generate involuntary EMG signals, or the electrical stimulation itself may be picked up as "false" EMG signals. To address this problem, in the illustrative embodiment the EMG/electrical stimulation hardware switch 24 enables time-domain multiplexing of the receive and transmit phases. That is, during message receive time intervals the switch 24 is set to connect the electrical stimulation transmitter 20 to the electrodes 14 and to simultaneously isolate the EMG readout circuitry 22 from the electrodes 14, and the message receive operations 50, 52, 54, 56, 58 are performed to receive messages via the radio transceiver 26 and convey them to the wearer via electrical stimulation patterns. During message transmit time intervals the switch 24 is set to connect the EMG readout circuitry 22 to the electrodes 14 and to simultaneously isolate the electrical stimulation transmitter 20 from the electrodes 14, and the operations 60, 62, 64, 66 are performed to transmit messages generated by the wearer (either volitionally or non-volitionally, depending on the type of message) via the radio transmitter 26. The transmit and receive time intervals are preferably separated by transition times on the order of a few milliseconds to a few tens of milliseconds to ensure that residual effects of the electrical stimulation do not interfere with the EMG signals. Moreover, the device can default to operating in the transmit mode in which EMG signals are monitored, and only switch to the receive mode when the RF transceiver 26 and RF signal processor 36 detect an incoming radio signal carrying a semantic message. Various other approaches for resolving transmit/receive conflicts are also contemplated, e.g. a radio 10 worn by a team leader may prioritize transmission over receive, whereas the radio 10 worn by a lower-level team member may prioritize receive over transmission. Dynamic reprioritization may also be performed based on content of the received and/or transmitted semantic messages, e.g. if a radio 10 worn by a military group member transmits a semantic message indicating weapon fire then that radio 10 may temporarily prioritize transmission (perhaps to the exclusion of performing the receive phase) for the duration of the weapons fire, as it may be most mission-critical to inform other team members of the active weapons fire.

In various embodiments, a high-density array of electrodes 14 on the forearm or other body part is used to both measure/decode muscle activity (i.e., EMG signals) to send commands and electrically stimulate haptic feedback (or other somatosensations, or FES) to receive information. This device enables efficient and intuitive bidirectional information transfer directly with the nervous system. The approach provides hyper-enabled capabilities including non-verbal and non-visual tactical communication, autonomous combat state monitoring, advanced navigational interfacing, and intelligent asset control, ultimately optimizing situational awareness and performance of team members who wear instances of the disclosed non-verbal communications radio 10.

Figure 3:
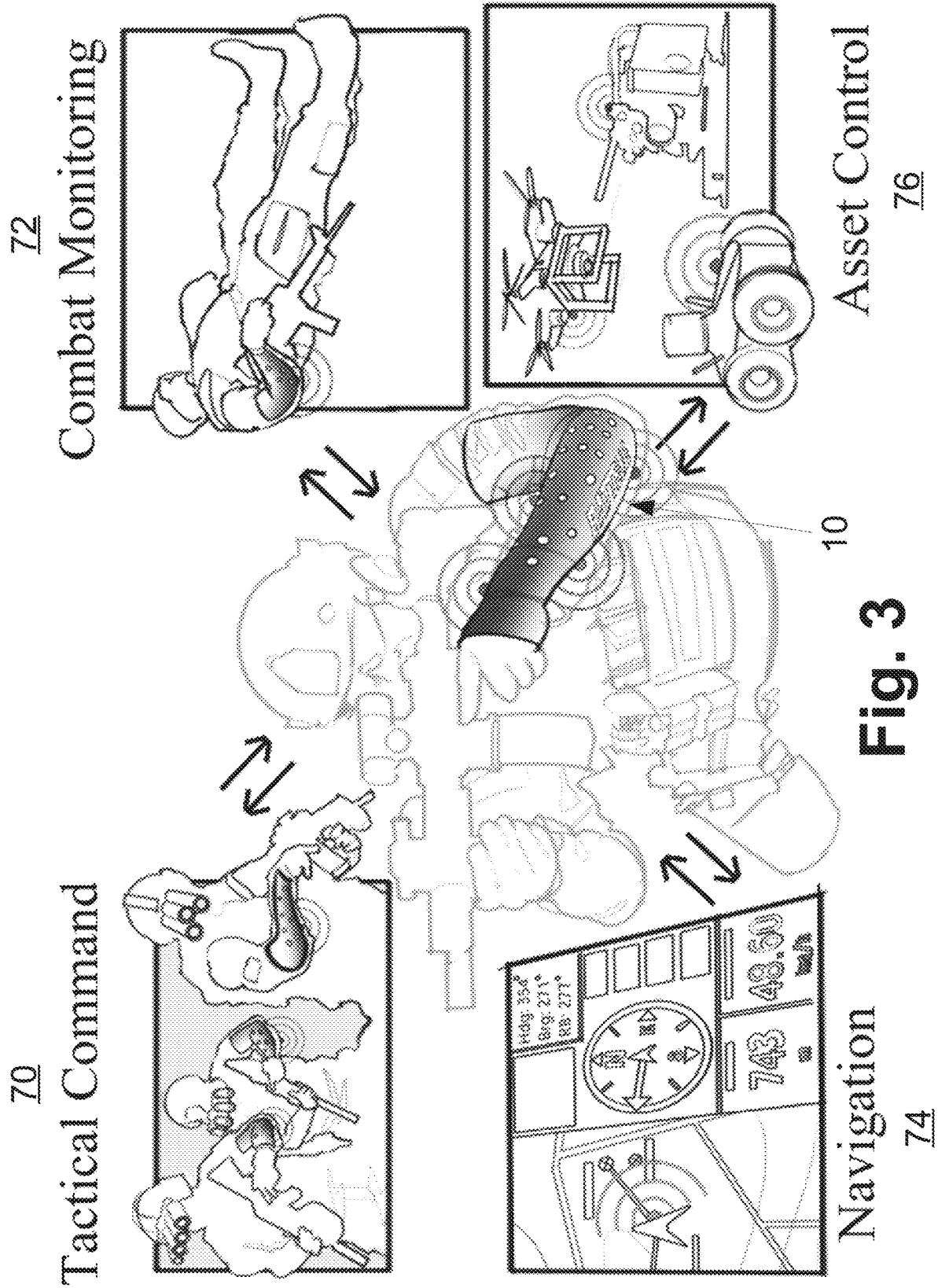
FIG. 3 diagrammatically shows four use cases of the non-verbal communications system of FIG. 1 in a special operations forces (SOF) application.

With reference now to FIG. 3, in one illustrative application for special operations forces (SOF), the disclosed non-verbal communications system provides command and control to every SOF component at every level of command. This technology enables real-time situational awareness (SA) and bi-directional communications within a squad, platoon, and company. By leveraging neural signals directly to and from the arm as a communications medium, the non-verbal communications radio 10 provides the operator a hands-free, non-verbal, non-visual communication capability, increasing the operator's SA while simultaneously reducing cognitive workload. Four potential use cases 70, 72, 74, 76 of the proposed non-verbal communications system for SOF support are described next as non-limiting examples.

The tactical command use case 70 is first described. In existing deployment approaches, the SOF use a variety of verbal and visual signaling to communicate tactical commands, such as motion, behavior, and confirmation/comprehension. However, these signals require SOF to communicate within a line of sight and in high-visibility conditions, often resulting in loss of weapon and target engagement during command. The disclosed non-verbal communications system addresses these issues by decoding commands from surface electromyography (sEMG) activity of one or multiple operators and relaying that information to other operators through patterned spatiotemporal haptic stimulation through the disclosed non-verbal communications radios 10, enabling silent, comprehensive communication. This system can enable rapid, hands-free communication through isometric or isotonic muscle contraction used to signal commands, alternative to full hand and arm movements or audible signals that may reveal SOF location during stealth missions.

The combat monitoring use case 72 is next described. Accessible intelligence regarding SOF combat and physiological state is valuable to squad members and command. This data enables critical and rapid tactical decision making, such as providing strategic backup. Additionally, SOF need to receive rapidly digestible information regarding adversary strategy and state of the mission. Here, combat monitoring and adversary state feedback capabilities are integrated into the disclosed non-verbal communications system. High-level combat monitoring, such as mission objectives, state of danger, and state of motion, communicated to SOF from remote command are indigestible during high-intensity operation because of the attention requirements of current communication devices. State of enemy attack can be communicated to SOF through the electro-tactile haptic capability of the non-verbal communications radios 10. The disclosed non-verbal communications system may also interpret SOF state of combat through the real-time measurement of sEMG, monitoring level of physical motion, signatures in the sEMG during weapon engagement, and stress levels indicated by muscle tenseness and fatigue. For example, the haptic feedback can vary in levels of distraction to indicate urgency of engagement.

The enhanced navigational interfacing use case 74 is next described. SOF operate in austere environments, often in conditions with minimal visibility and in zones with restricted communications. Hyper Enabled Operators (HEO) require the ability to navigate all types of environments effectively. Here navigation feedback and control capabilities are integrated into the disclosed non-verbal communications system to enable navigation technology that is relayed directly into the operator's arm via the garment 12. This capability will extend the current SOF navigation abilities by providing hands-free directional information and navigational control. The disclosed non-verbal communications radios 10 will receive navigational information such as the target direction, which can then be interpreted to create a relative directional vector that can be mapped to the arm. Using the sEMG capabilities, gestures can be used for navigational control such as pointing in a specific direction or performing a particular movement to begin/end navigation. By projecting navigational information into direction vectors using intelligent electro-tactile haptic stimulation patterns will revolutionize how operators receive location information of squad members, target locations, enemy locations, and asset locations, thus hyper-enabling operators.

Finally, the intelligent asset control use case 76 is described. Special operation forces are often reliant on various assets for successful mission outcomes, and interfacing with these assets requires substantial cognitive overhead. In order to reduce cognitive overload, the disclosed non-verbal communications system integrates control of various assets. The integration will allow SOF to control UAVs and ground vehicles while simultaneously receiving state information about the asset. The disclosed non-verbal communications radio 10 will provide the operator with spatiotemporal electro-tactile haptic information about the state of the assets, and also allow the operator to provide specific commands to the asset through patterned muscle activity of the arm and hand.

The disclosed non-verbal communications radios 10 facilitate command and control to every SOF component at every level of command. This technology enables real-time situational awareness (SA) and bi-directional communications within a squad, platoon, and company. By leveraging neural signals directly to and from the arm as a communications medium, the SOCS system provides the operator a hands-free, non-verbal, non-visual communication capability, increasing the operator's SA while simultaneously reducing cognitive workload.

In the context of the combat monitoring use case 72 of FIG. 3, other types of information may be usefully conveyed via the disclosed non-verbal communications radios 10. The sleeve 10 thus serves as a sensor, and the communication on the other end can be received as a somatosensory signal delivered by the receiving sleeve, or by vibrotactile, visual, audible, or other human-perceptible signal. Likewise, the sleeve 10 could receive tactile, visual, computer keyboard, or audible signal that is then transmitted to the wearer of the sleeve as somatosensory stimulus. This allows, for example, for a command center to use verbal or computer commands to send information to the sleeve wearer.

For example, if a squad member is injured, sensors of the non-verbal communications radio 10 may be used to acquire information on both the physical state of the injured squad member and the severity of the injury. For example, sensors measuring heart rate, body temperature, or other vital signs may be included in the radio 10 and these vital sign readings may be included in the transmitted radio signals. Even more, three-dimensional (3D) electrical impedance tomography (EIT) may be performed using the high-density array of electrodes 14 of the radio 10 to obtain an image of the injured body part of the squad member. EIT can provide useful information in the event of an injury such as a stroke, spinal cord injury, bone fracture, or so forth. For example, EIT may be useful to identify the location of a broken bone. Processing of the electrical impedances measured by the high-density array of electrodes 14 to reconstruct a 3D image is computationally complex, and may be impractical using the electronics module 16 of the garment 12 which typically has a microprocessor of low power draw and hence limited computational capacity. Hence, in some embodiments, the (raw) electrical impedances measured by the high-density array of electrodes 14 to acquire the EIT image are transferred via the radio transceiver 26 of the injured squad member's radio 12, and these raw electrical impedances are received by a radio of a base station computer (or other computer; not shown) which has the computational capacity to reconstruct the EIT image for review by a medical expert at the base station. Additionally or alternatively, the raw electrical impedances may be fed into a pre-trained injury classifier (e.g. trained offline on a training set of persons with/without that type of injury) to classify the injury (e.g., sprain or bone fracture). As the classifier is pre-trained, this approach may be feasibly implemented at the electronics module 16 of the garment 12.

The disclosed non-verbal communications radios 10 can be employed in a wide range of other applications. Some further applications are described below.

Figure 4:
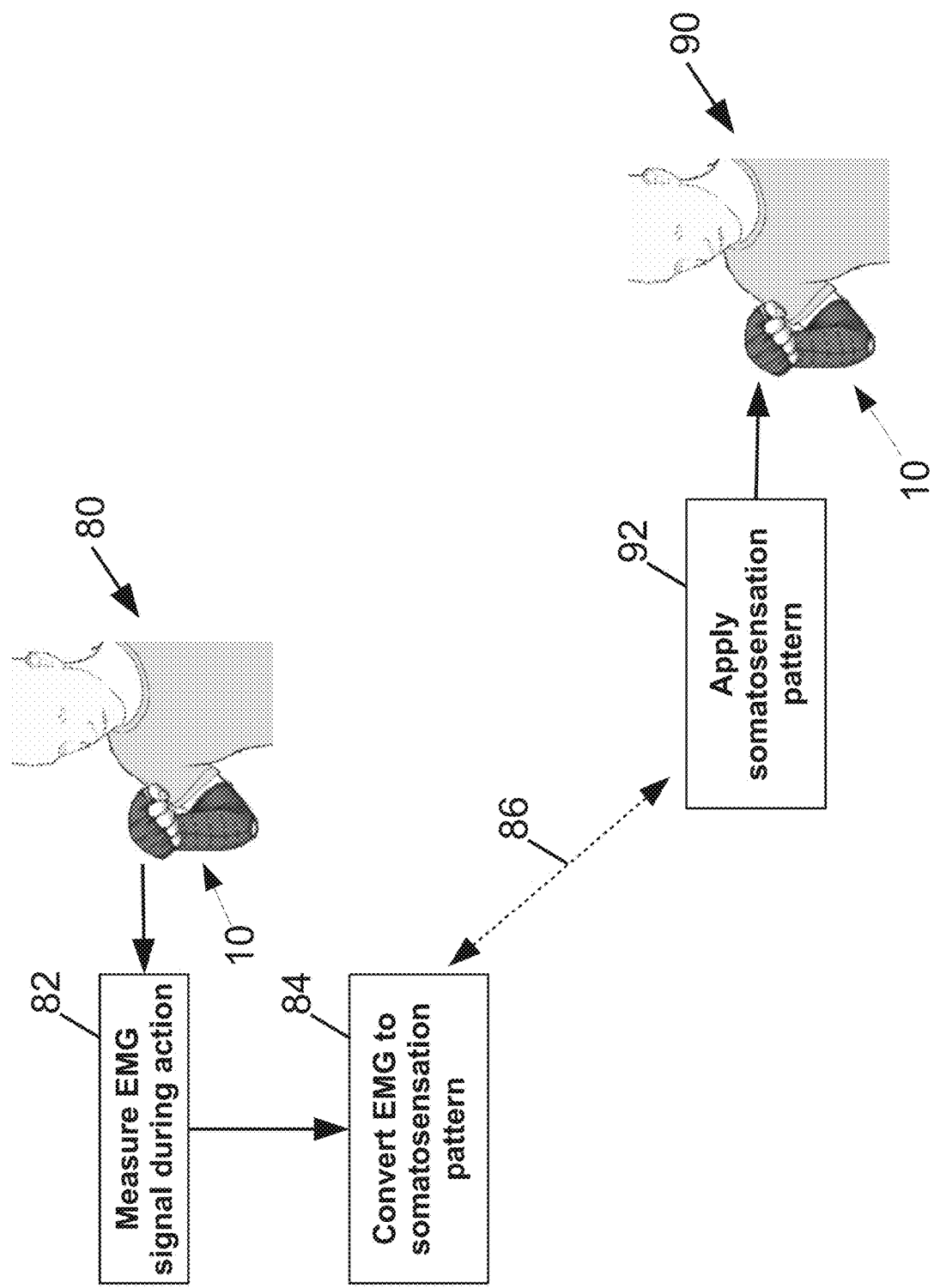
FIG. 4 diagrammatically shows a use case of the non-verbal communications system of FIG. 1 for training.

With reference to FIG. 4, in some applications, non-verbal communications radios 10 are used to in a training setting or in motor skill transfer, to convey information from one user to another user. For example, in a multiplayer gaming setting, gamers can help each other using EMG or some motion sensing acquired by the garment 12, and the sensation is transferred to another gamer via their garment 12 to guide them toward better performance. This provides hints using somatosensory stimulation provided by the garment 12. As an example, FIG. 4 depicts a first user 80 (also sometimes referred to herein as an "expert") who performs a first motor action (e.g., a controller operation on a gaming controller, or a golf swing in the case of a golfing setting, or some other action performed during a sports activity or so forth. The expert 80 wears an expert wearable device 10 comprising the non-verbal communications radio 10 (this instance of the radio 10 is also sometimes referred to herein as an "expert wearable device"). As the first user 80 performs the action, in an operation 82 EMG signals generated by the relevant muscles are recorded by the high-density array of electrodes 14 of the expert wearable device 10. In an optional operation 84, the recorded EMG may be scaled in intensity, spectrally filtered, or otherwise processed to provide a somatosensation pattern. The recorded EMG either as-recorded (i.e. directly from step 82) or after the optional processing 84, then serves as the message to be transmitted to a second instance of the non-verbal communications radio 10 worn by a second user 90 (This instance of the non-verbal communications radio 10 is sometimes referred to herein as a "learner wearable device). Note that in the embodiment of FIG. 4, the semantic database 40 of FIG. 1 is not used; rather, the recorded or recorded-and-processed EMG serves as the message. This signal is then transmitted from the expert wearable device to the learner wearable device as a radio signal encoding the outgoing recorded or recorded-and-processed EMG. The signal is transmitted using the radio transceiver 26 of the learner wearable device 10 of the expert 80 to the learner wearable device 10 of the learner 90. (This radio transmission is diagrammatically indicated by dotted connecting arrow 86). At the second user, in an operation 92 the received radio signal is processed (e.g. demodulated) to extract the signal (which again is the EMG of the first user 80 recorded at operation 82 and optionally processed at operation 84) and is applied to the corresponding muscles of the second user 90 via the high-density array of electrodes 14 of the second user's non-verbal communications radio 10.

The type of transfer of muscle activity from one user to another as a somatosensation, as described with reference to FIG. 4, can be applied in numerous situations. For example, it may be used in conjunction with activity that involves manipulation of an object, such as a ballplayer swinging a bat or a pitcher throwing a ball or a woodworker swinging an axe, or so forth. Optionally, in such an embodiment the EMG acquired in operation 82 may be augmented by acquired information about the contact with the object. For example, in the case of a ball player swinging a bat, the garment 12 worn by the first user 80 may include a batter's glove that has built-in pressure sensors, and the contact with the bat during the swing may be acquired using the pressure sensors. The object itself may also include sensors, e.g. an accelerometer mounted on the bat may measure the swing action and the impact of the ball onto the bat (assuming the swing is a hit). These other sensor signals can be transmitted as part of the radio transmission 86, and may be applied by corresponding sensors of the garment 12 worn by the second user 90 (and/or corresponding sensors mounted on a bat or other corresponding object manipulated by the second user 90. For example, the impact of the ball onto the bat can be simulated for the second user 90 by a force sensor mounted on the bat held by the second user 90.

Such usage of the non-verbal communications radios 10 may find particular use in sports training, by enforcing repetitive motion for sub-conscious neuro-muscular training based on the proper motion measured from an expert user. This encourages and trains the second user 90 to engage the correct muscle groups to help counterbalance bad form. The approach can be used to attain the perfect golf swing or free throw shoot. Other applications may include training an actor to play a particular role or act a particular movie scene—in this case the actor-in-training is the second user 90, and the first user 80 is a more senior actor with more experience in playing that role or acting that scene. Similarly, a pianist or other musician can learn to play a particular musical piece. Here the musician-in-training is the second user 90 and a music teacher may be the first user 80. The high-density array of electrodes 14 of the garment 12 (here, a glove) worn by the musician-in-training 90 is energized at an FES level to evoke fingers to play a virtual or real piano, or is energized at a lower level to provide somatosensation to specific fingers as cues to train the musician-in-training in the fingering of the piece. Similar approaches can be used in learning other musical instruments such as wind instruments, brass instruments, or so forth.

In the description of FIG. 4, it was described that the radio transmission 86 is performed in real-time. This can be beneficial as the learner 90 can directly observe and attempt to mimic in real time the action performed by the expert 80, with the somatosensation applied at operation 92 providing assistance. However, the transfer of the EMG recorded at operation 82 (or that EMG after processing per operation 84) to the radio 10 of the second user 90 can be delayed, or even replaced by some other type of transmission mode.

For example, in another contemplated approach, the first user 80 is an expert (for example, a professional golfer) who performs the action (e.g., golf swing) while operation 82 and optional operation 84 generate the somatosensation pattern. The somatosensation pattern is then stored on a non-transitory storage medium (e.g. flash drive, uploaded to a storage of an Internet-based server computer, et cetera). Optionally, the expert 80 may be video recorded while performing the action. Thereafter (e.g., days, weeks, or longer after), a novice golfer can purchase the garment 12 and "replay" the somatosensation pattern per operation 92, optionally while also watching the prerecorded video of the expert performing the golf swing. In this approach, the radio transmission 86 is suitably performed at the time of sale of the garment 12 to the second user 90 in order to load the somatosensation into the non-transitory storage of the electronics module 16 of the garment 12 purchased by the second user 90. Indeed, in this embodiment, the radio transmission 86 could be replaced by some other method for transferring the somatosensation generated at operation 84 to garment 12 of the second user 90, such as being transferred using a flash drive, micro-SD card, or other physical storage medium. Or, the radio transceivers 26 in this embodiment may be WiFi radios that connect the radios 10 with the Internet, and the somatosensation generated at operation 84 can be stored at a server-based website and later downloaded to the garment 12 of the second user 90 via the Internet. In this way, an Internet-based repository of somatosensations can be developed for various motor skills (e.g. bat swings, golf swings, baseball pitches, weightlifting actions, et cetera), which can then be downloaded to an end-user's garment 12 as desired.

In the embodiment of FIG. 4 and variants thereof just described, it will be appreciated that the somatosensation may be used in various ways. For example, in the operation 92, instead of automatically applying the somatosensation via the garment 12 of the second user 90, the high-density array of electrodes 14 of the garment 12 of the second user 90 may be used to measure the EMG signals produced by the second user 90 when attempting to perform the action. These EMG signals measured from the second user 90 can then be compared against the ideal "template" EMG signals previously acquired from the expert 80 at the operation 82. If the second user's measured EMG deviates significantly from this template, then the high-density array of electrodes 14 of the second user's garment 12 may be used to apply the (from operation 82 and optional operation 84) to indicate the form error at the musculature of the second user where the motor action error is occurring. Alternatively, the high-density array of electrodes 14 of the second user's garment 12 may be used to apply the somatosensation at a higher amplitude so as to generate actual FES (that is, function electrical stimulation) that actually corrects the motor action of the second user 90.

In such skill learning approaches, the amount of guidance (e.g., the magnitude of the somatosensation applied to the second user 90) or the kind of guidance (e.g., merely somatosensation or FES to cause actual muscle action) is optionally adapted to the user's skill level to provide progressively more precise feedback or stimulate progressively more advanced movements. The amount or kind of guidance might also be a (second) user-selectable option—for example, some (second) users 90 may not be comfortable receiving FES and may select only a mild somatosensation.

Figure 5:
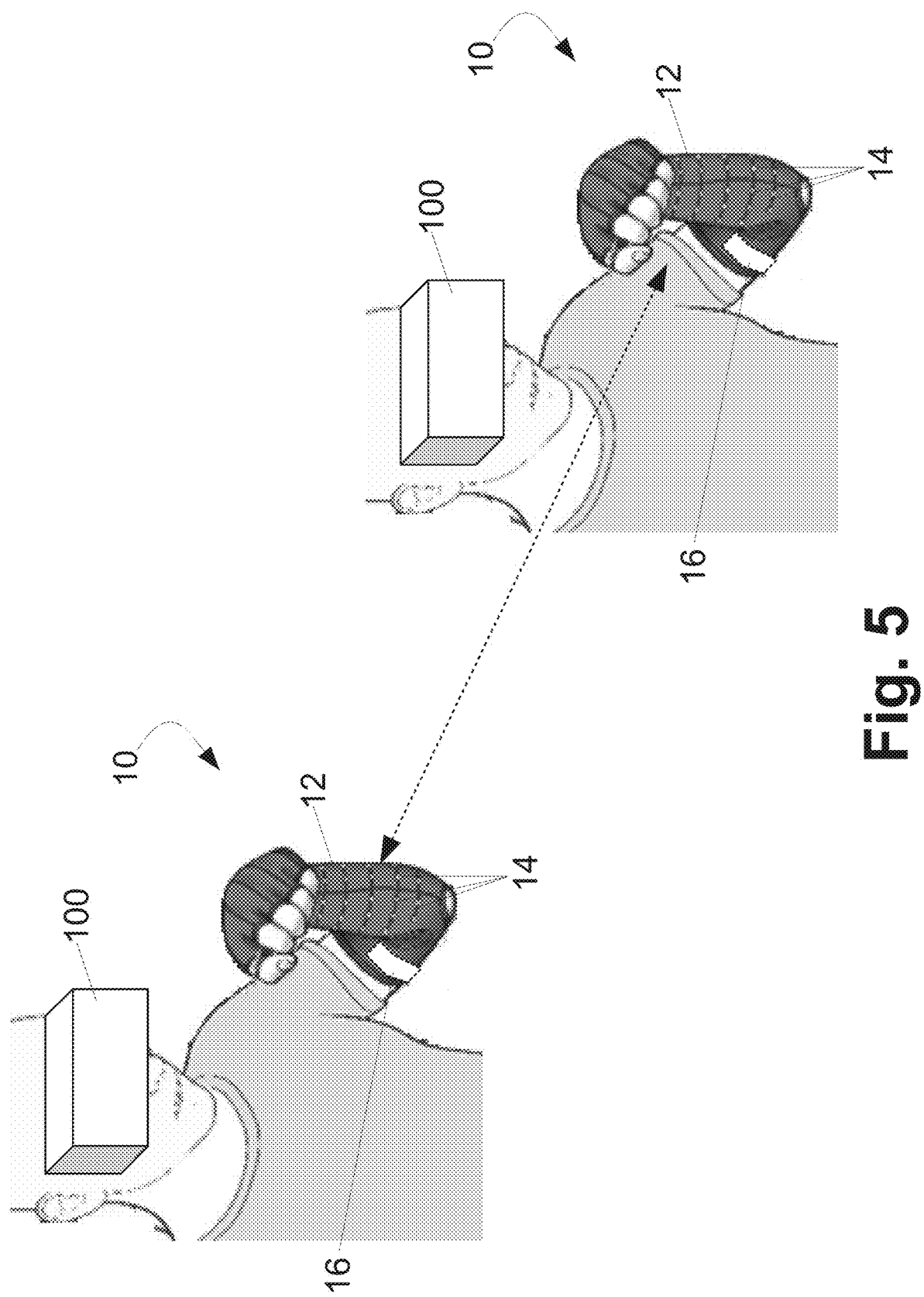
FIG. 5 diagrammatically shows a use case of the non-verbal communications system of FIG. 1 in conjunction with a virtual reality (VR) or augmented reality (AR) headset.

With reference to FIG. 5, in other embodiments this approach of conveying somatosensations between users via the disclosed non-verbal communications radios 10 is usefully employed in conjunction with a virtual reality (VR) or augmented reality (AR) system. the VR system includes a VR headset 100 for presenting audio-visual elements of the VR or AR environment to the user. Other sensors (beside the EMG readout 22) may be included in the VR or AR headset 100, such as accelerometers to track head motion, gaze sensors to detect gaze direction and distance, and so forth. The VR or AR system can be used to simulate audio-visual elements of a virtual or augmented environment for applications such as VR videogaming, work setting simulators for employee training, enhanced reality audio-video presentations (e.g. movies), and the like. In the case of AR, the headset 100 provides partial perception of the real world with superimposed augmented reality features. For example, the headset 100 when used for AR may include eyeglasses, goggles, or the like with transparent lenses that allow the user to see the real world, but in which those transparent lenses have integrated translucent displays that permit superimposing AR elements onto the real world view.

The integration of the disclosed non-verbal communications radios 10 into a VR or AR system implemented using (at least) the headset 100 substantially expands the use cases of the disclosed non-verbal communications radios 10. Some examples follow.

In one example, a quarantine patient may utilize the combination to provide more intimate visitation with relatives or friends who are unable to physically enter the quarantine environment. With the combined system, the non-verbal communications radio 10 can add a sense of touch to a VR or AR visitation experience. For example, in a child quarantine situation, a parent or grandparent can physically feel a hug from their grandchild (implemented as somatosensations delivered by the high-density array of electrodes 14) when looking through a window in their presence. Indeed, with such a system but using full VR, two people in completely different locations can interact with each other with senses of sight, sound, and touch.

Another use case is in the field of telemedicine. For example, a difficulty in telemedicine is that it can be difficult for a patient to convey symptoms such as pain to the physician. With the present approach, if both the patient and the physician are wearing instances of the (same) garment 12, then different pain somatosensations simulating different types and/or levels of pain can be delivered sequentially to the patient and the physician, and the patient can then identify which of these pain somatosensations most accurately matches the actual pathology pain being experienced by the patient. (It should be noted that "pain" as used in this embodiment may broadly encompass any type of discomfort caused by a pathology, e.g. acute pain, numbness, sensation of heat or cold, muscle soreness, et cetera). In this way, the physician obtains a realistic impression of the pain being experienced by the patient. (Indeed, this approach could even be useful in an in-person physician's office visit). For this approach to work, the patient suitably wears a patient wearable device 10 and the physician wears a physician wearable device 10, and the patient wearable device and the physician wearable device are in communication so as to apply the same somatosensation pattern at the same time using both the patient wearable device and the physician wearable device. The communication can be by the illustrative radio transceiver 26 of FIG. 1 if the two wearable devices are close enough for radio transmissions (likely to be the case for an in-person physician's office visit, and possibly also for a remote diagnosis of a quarantined patient in a situation where the physician does not actually enter the quarantine room but may be in an adjacent room). For telemedicine applications where the patient and physician may be much further apart (e.g. different buildings, different cities, different states or even different countries), the patient wearable device and the physician wearable device may be in communication by way of being both connected via the Internet to a same website that simultaneously provides each pain somatosensation pattern to both wearable devices.

In a variant approach, if only the patient is wearing an instance of the garment 12 (but the physician is not) then different pain somatosensations simulating different types and/or levels of pain retrieved from a library of annotated pain somatosensations (e.g., stored on a non-transitory storage medium) can be delivered sequentially to the patient alone (not to the physician). Again, the patient identifies which of these pain somatosensations most accurately matches the actual pathology pain being experienced by the patient. Each pain somatosensation of the library of annotated pain somatosensations is annotated with a corresponding pathology or pathologies that produce that type/level of pain, and the physician can then use the annotation as part of the information upon which a diagnosis may be based.

In this embodiment, the library of annotated pain somatosensations would be developed offline (i.e. prior to the telemedicine or in-person physician's visit). Each somatosensation is suitably tuned to match a type and level of pain experienced by a reference patient. This can be done by delivering the somatosensation and receiving guidance for adjusting from the reference patient (e.g., my pain is less intense; or my pain is over a larger area; or so forth). Once the applied somatosensation closely matches the reference patient's actual pathology pain, then the tuned pain somatosensation is stored in the library with an annotation of the pathology of the reference patient. By doing this for a large number of reference patients with different pathologies, the library of annotated pain somatosensations can be made comprehensive and usable for diagnosing patients with a wide range of different pathologies.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A communications radio comprising:
an array of electrodes configured to be disposed on a body part;
a radio transceiver;
an electrical stimulation transmitter operatively coupled with the array of electrodes;
electromyography (EMG) receive circuitry operatively coupled with the array of electrodes; and
a data processing sub-module configured to perform radio communication including (i) using the electrical stimulation transmitter and the array of electrodes, presenting semantic messages received via the radio transceiver as electrical stimulation patterns, and (ii) via the radio transceiver, transmitting semantic messages determined from EMG signals measured using the array of electrodes and the EMG receive circuitry.

2. The communications radio of claim 1 wherein the data processing sub-module includes an electronic processor and a non-transitory storage medium storing instructions readable and executable by the electronic processor to:
(i) receive a radio signal via the radio transceiver, determine a semantic message from the received radio signal, encode an electrical stimulation pattern representing the semantic message determined from the received radio signal, and apply the electrical stimulation pattern using the electrical stimulation transmitter and the array of electrodes, and to
(ii) receive EMG signals via the array of electrodes and the EMG receive circuitry, determine a semantic message from the EMG signals, encode a radio signal representing the semantic message determined from the EMG signals, and transmit the encoded radio signal via the radio transceiver.

3. The communications radio of claim 2 wherein the non-transitory storage medium further stores a semantic database containing:
information for determining the semantic message from the received radio signal and for encoding the electrical stimulation pattern representing the semantic message determined from the received radio signal, and
information for determining the semantic message from the EMG signals.

4. The communications radio of claim 3 wherein:
the information for determining the semantic message from the received radio signal comprises at least one look-up table that associates radio signals with corresponding semantic messages; and/or
the information for encoding the electrical stimulation pattern representing the semantic message determined from the received radio signal comprises at least one look-up table that associates semantic messages with corresponding spatiotemporal electrical stimulation patterns; and/or
the information for determining the semantic message from the EMG signals comprises parameters of an EMG decoder implemented as a machine learning component trained to translate received EMG signals into corresponding semantic messages.

5. The communications radio of claim 1 further comprising:
a garment wearable on the body part with the array of electrodes in electrical contact with skin of the body part.

6. The communications radio of claim 1 wherein the radio transceiver is one of:
a single radio transceiver having both transmit and receive capability; or
separate radio receiver and radio transmitter components that together form the radio transceiver.

7. The communications radio of claim 1 wherein the transmitted semantic messages determined from EMG signals measured using the array of electrodes and the EMG receive circuitry include semantic messages conveying navigational information.

8. The communications radio of claim 1 wherein the data processing sub-module is further configured to:
acquire three-dimensional electrical impedance tomography (3D-EIT) imaging data using the array of electrodes and to transmit the acquired 3D-EIT imaging data using the radio transceiver.

9. A communications radio comprising:
an array of electrodes configured to be disposed on a body part;
a radio transceiver;
an electrical stimulation transmitter operatively coupled with the array of electrodes;
electromyography (EMG) receive circuitry operatively coupled with the array of electrodes; and
a data processing sub-module configured to perform radio communication including (i) using the electrical stimulation transmitter and the array of electrodes, presenting semantic messages received via the radio transceiver as electrical stimulation patterns, and (ii) via the radio transceiver, transmitting semantic messages determined from EMG signals measured using the array of electrodes and the EMG receive circuitry, wherein the data processing sub-module is configured to perform time domain multiplexing in which:
(i) during a receive time interval the electrical stimulation transmitter is operatively connected to the array of electrodes to present semantic messages received via the radio transceiver as electrical stimulation patterns, and
(ii) during a transmit time interval the EMG receive circuitry is operatively connected to the array of electrodes to transmit semantic messages determined from EMG signals measured using the array of electrodes and the EMG receive circuitry.

10. The communications radio of claim 9 further comprising an EMG/electrical stimulation switch operative to (i) switch to connect the EMG receive circuitry to the array of electrodes and simultaneously isolate the electrical stimulation transmitter from the array of electrodes, and (ii) switch to connect the electrical stimulation transmitter to the array of electrodes and simultaneously isolate the EMG receive circuitry from the array of electrodes.

11. A communication system comprising:
a plurality of wearable communications radios configured to provide nonverbal communication between persons wearing the respective wearable communications radios;
wherein each wearable communications radio includes:
an array of electrodes configured to be disposed on a body part;
a radio transceiver;
an electrical stimulation transmitter operatively coupled with the array of electrodes;
electromyography (EMG) receive circuitry operatively coupled with the array of electrodes; and
a data processing sub-module configured to perform radio communication including (i) using the electrical stimulation transmitter and the array of electrodes, presenting semantic messages received from at least one other wearable communication radio of the plurality of wearable communication radios via the radio transceiver as electrical stimulation patterns, and (ii) via the radio transceiver, transmitting semantic messages determined from EMG signals measured using the array of electrodes and the EMG receive circuitry to at least one other wearable communication radio of the plurality of wearable communication radios.

12. The communication system of claim 11 further comprising:
an unmanned aerial vehicle (UAV) having a radio configured to communicate with at least one radio of the plurality of communications radios;
wherein the transmitted semantic messages determined from EMG signals measured using the array of electrodes and the EMG receive circuitry include semantic messages for controlling the UAV; and
wherein the semantic messages presented as electrical stimulation patterns include semantic messages received from the UAV via the radio transceiver.

13. The communication system of claim 11 wherein each wearable communications radio further includes a garment wearable on the body part with the array of electrodes in electrical contact with skin of the body part.

14. The communications system of claim 11 wherein the data processing sub-module of each wearable communications radio includes an electronic processor and a non-transitory storage medium storing instructions readable and executable by the electronic processor to:
(i) receive a radio signal from another wearable communication radio of the plurality of wearable communication radios via the radio transceiver, determine a semantic message from the received radio signal, encode an electrical stimulation pattern representing the semantic message determined from the received radio signal, and apply the electrical stimulation pattern using the electrical stimulation transmitter and the array of electrodes, and to
(ii) receive EMG signals via the array of electrodes and the EMG receive circuitry, determine a semantic message from the EMG signals, encode a radio signal representing the semantic message determined from the EMG signals, and transmit the encoded radio signal via the radio transceiver to at least one other wearable communication radio of the plurality of wearable communication radios.

15. The communications system of claim 11 wherein the data processing sub-module of each wearable communications radio is configured to perform time domain multiplexing in which:
(i) during a receive time interval the electrical stimulation transmitter is operatively connected to the array of electrodes to present semantic messages received via the radio transceiver as electrical stimulation patterns, and
(ii) during a transmit time interval the EMG receive circuitry is operatively connected to the array of electrodes to transmit semantic messages determined from EMG signals measured using the array of electrodes and the EMG receive circuitry.

16. A radio communications method comprising:
presenting a received semantic message by operations including receiving a radio signal using a radio transceiver, determining the received semantic message from the received radio signal, and applying an electrical stimulation pattern to a body part wherein the electrical stimulation pattern represents the semantic message determined from the received radio signal; and
sending an outgoing semantic message by operations including receiving electromyography (EMG) signals, determining the outgoing semantic message from the EMG signals, and transmitting the outgoing semantic message as a radio signal encoding the outgoing semantic message and transmitted using the radio transceiver.

\* \* \* \* \*